United States Patent
Norman

(10) Patent No.: US 9,522,056 B2
(45) Date of Patent: Dec. 20, 2016

(54) METHOD AND APPARATUS FOR DEVICE FOR BRUSHING TEETH

(71) Applicant: Vincent Norman, North Bergen, NJ (US)

(72) Inventor: Vincent Norman, North Bergen, NJ (US)

( * ) Notice: Subject to any disclaimer, the term of this patent is extended or adjusted under 35 U.S.C. 154(b) by 0 days.

(21) Appl. No.: 14/665,546

(22) Filed: Mar. 23, 2015

(65) Prior Publication Data

US 2016/0278898 A1 Sep. 29, 2016

(51) Int. Cl.
*A61C 17/34* (2006.01)
*A61C 17/40* (2006.01)
*F16H 21/50* (2006.01)
*F16H 21/48* (2006.01)

(52) U.S. Cl.
CPC ............ *A61C 17/3472* (2013.01); *A61C 17/40* (2013.01); *F16H 21/48* (2013.01); *F16H 21/50* (2013.01); *A61C 17/3418* (2013.01); *A61C 17/3445* (2013.01)

(58) Field of Classification Search
CPC ............ A61C 17/3445; A61C 17/3418; A61C 17/3472; A61C 17/3409
USPC .................................................. 15/22.2, 22.4
See application file for complete search history.

(56) References Cited

U.S. PATENT DOCUMENTS 4,710,995 A * 12/1987 Joyashiki ........... A61C 17/3445
15/22.1
5,448,792 A * 9/1995 Wiedemann ........... A61C 17/34
15/22.1

* cited by examiner

*Primary Examiner* — Laura C Guidotti
(74) *Attorney, Agent, or Firm* — Walter J. Tencza, Jr.

(57) ABSTRACT

An apparatus and method including a toothbrush head; toothbrush bristles fixed to the toothbrush head; and means for moving the toothbrush head in up and down directions and for simultaneously rotating the tooth brush head in a plane which is perpendicular to the up and down directions. The means for moving the toothbrush head in the up and down directions and for simultaneously rotating the tooth brush head in the plane which is perpendicular to the up and down directions may include a motor, a motor shaft, a disk, a swing arm, a post, and a pin. The apparatus may be configured so that the motor rotates the motor shaft causing the disk to rotate causing the pin to move in the up and down directions and causing the swing arm to rotate in the plane which is perpendicular to the up and down directions.

19 Claims, 2 Drawing Sheets

METHOD AND APPARATUS FOR DEVICE
FOR BRUSHING TEETH

FIELD OF THE INVENTION

This invention relates to improved methods and apparatus concerning tooth brushing devices.

BACKGROUND OF THE INVENTION

There are various devices known in the prior art for brushing teeth. Various motorized tooth brushes are known. For example, the known Sonic (trademarked) tooth brush moves up and down and thereby undesirably pushes plaque, bacteria, and waist into the gums of an individual. The known Oral B (trademarked) tooth brush does not cover enough area and therefore requires too much work to brush someone's teeth.

SUMMARY OF THE INVENTION

In at least one embodiment of the present invention an apparatus is provided for brushing teeth which creates an oval motion, which is generally speaking the type of motion that dentists recommend to use while someone is brushing their teeth.

In at least one embodiment of the present application an apparatus is provided which combines two motions in one, not only pulling wastes out of someone's gum line like the Oral B (trademarked) but also covering enough surfaces on someone's teeth to make brushing less work.

In at least one embodiment an apparatus is provided comprising a toothbrush head; toothbrush bristles fixed to the toothbrush head; and means for moving the toothbrush head in up and down directions and for simultaneously rotating the tooth brush head in a plane which is perpendicular to the up and down directions. The means for moving the toothbrush head in the up and down directions and for simultaneously rotating the tooth brush head in the plane which is perpendicular to the up and down directions may include a motor, a motor shaft, a disk, a swing arm, a post, and a pin.

The apparatus may be configured so that the motor rotates the motor shaft causing the disk to rotate causing the pin to move in the up and down directions and causing the swing arm to rotate in the plane which is perpendicular to the up and down directions. The movement of the pin up and down may cause the post to move up and down which causes the toothbrush head to move up and down. The rotation of the swing arm in the plane which is perpendicular to the up and down directions may cause the post to rotate in the plane which is perpendicular to the up and down directions which may cause the toothbrush head to rotate in the plane which is perpendicular to the up and down directions. The disk may include first and second ramp portions which cause the pin to move in the up and down directions as the disk rotates.

A method is also provided which may include using a motor to move a toothbrush head having toothbrush bristles fixed thereto in up and down directions and to simultaneously rotate the tooth brush head in a plane which is perpendicular to the up and down directions. The motor may turn a motor shaft which rotates a disk causing a pin to move in the up and down directions which causes a swing arm to rotate in the plane which is perpendicular to the up and down directions. The movement of the pin up and down may cause a post to move up and down which causes the toothbrush head to move up and down. The rotation of the swing arm in the plane which is perpendicular to the up and down directions causes the post to rotate in the plane which is perpendicular to the up and down directions which causes the toothbrush head to rotate in the plane which is perpendicular to the up and down directions. The disk may include first and second ramp portions which cause the pin to move in the up and down directions as the disk rotates. The method may further include brushing a person's teeth with the toothbrush bristles.

DETAILED DESCRIPTION OF THE DRAWINGS

Figure 1:
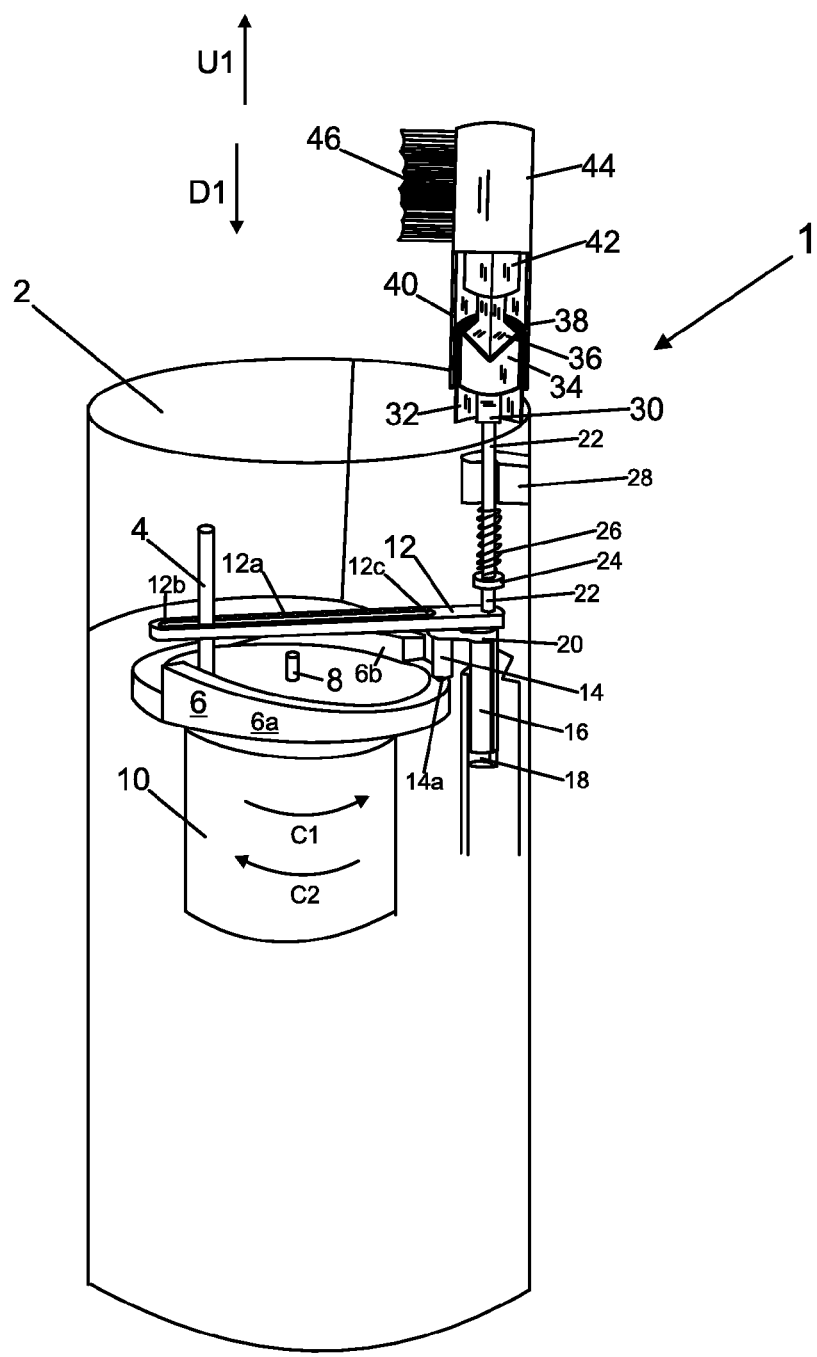
FIG. 1 shows a perspective view of an apparatus in accordance with an embodiment of the present invention with part of the apparatus shown as transparent so that various components can be seen, and some parts of the apparatus cut away or only a section shown, so that inner components can be seen.

FIG. 1 shows a perspective view of an apparatus 1 in accordance with an embodiment of the present invention with part of the apparatus 1 shown as transparent so that various components can be seen. Also part of the apparatus 1 is cut away so that various components can be seen as will be described.

The apparatus 1 includes a tooth brush chassis or body portion 2, a swing arm shaft 4, a disk 6, a motor shaft 8, a motor 10, a swing arm 12, a pin 14, a ball 14a, a push leg 16, a cylinder mount 18, a connecting member 20, a spring post 22, a washer 24, a spring 26, a clip 28, a bottom axle 30, a bottom cylinder 32, a square axle boot 34, a square axial leg 36, a bottom axle boot lip 38, a tooth brush head cylinder 40, a square axle 42, a tooth brush head 44, and tooth brush bristles 46. The clip 28 attaches the spring post 22 to the body portion 2.

FIG. 1 shows only a cut away or section of the tooth brush head cylinder 40 so that inner components can be seen. FIG. 1 shows only a cut away or section of the bottom cylinder 32 so that inner components can be seen.

The disk 6 includes ramp portions 6a and 6b. The ramp portion 6a increases from a minimum level near a maximum level of ramp portion 6b to a maximum level near a minimum level of ramp portion 6b. The swing arm 12 includes a slot 12a. The slot has an end 12c and an opposing end 12b. The swing arm shaft 4 is fixed to the disk 6.

In operation, the motor 10 rotates the shaft 8 which causes rotation of the disk 6 in the counter clockwise direction C1. The rotation of the disk 6, in the counterclockwise direction C1 from the position of FIG. 1, causes the pin 14a to rise as the part of the ramp portion 6a on which the pin 14a sits changes from near a minimum level to a maximum level for the ramp portion 6a. This also causes the swing arm shaft 4 to effectively slide in the slot 12a from the position in FIG. 1 near the end 12b towards the end 12c. This also causes the swing arm 12 to rotate, at first in the counter clockwise direction C1. The swing arm shaft 4, keeps effectively sliding in the slot 12a until the shaft 4 reaches the end 12c or near the end 12c. At about the same time, disk 6 has rotated until the ramp portion underneath the ball 14a is at the maximum. Then the pin 14a effectively falls off of the ramp portion 6a and onto the minimum level of the ramp portion 6b. At about the same time, the shaft 4 begins effectively sliding back towards the end 12b, and the swing arm 12 rotates back in the clockwise direction C2, shown in FIG. 1. As the motor 10 keeps turning the motor shaft 8 and the disk 6, the cycle repeats itself with the swing arm 12 being rotated back and forth in the directions C1 and C2. The rotation back and forth of the swing arm 12 causes the spring post 22 to rotate back and forth which causes the bottom axle 30 which is fixed to the spring post 22 to rotate back and forth in the directions C1 and C2, which causes the the square axle boot 34 to rotate back and forth, which causes the square axial leg 36 to rotate back and forth, which causes the square axle 42 to rotate back and forth, which causes the tooth brush head 44 and tooth brush head cylinder 40 to rotate back and forth, which causes the bristles 46 to rotate back and forth in directions C1 and C2. The tooth brush head 44 may be the same as the tooth brush head cylinder 40.

In addition as the pin 14a level rises and falls on the ramp 6, this causes the arm 12 level to rise up in the direction U1 and fall in the direction D1, which causes the tooth brush head 44 and/or cylinder 40 to rise up and down in the directions U1 and D1, respectively. Thus the toothbrush head 44 and/or cylinder 40 is rotated back and forth in the counter clockwise direction C1 and the clockwise direction C2, respectively, and pushed up and down in the directions U1 and D1, respectively.

Figure 2:
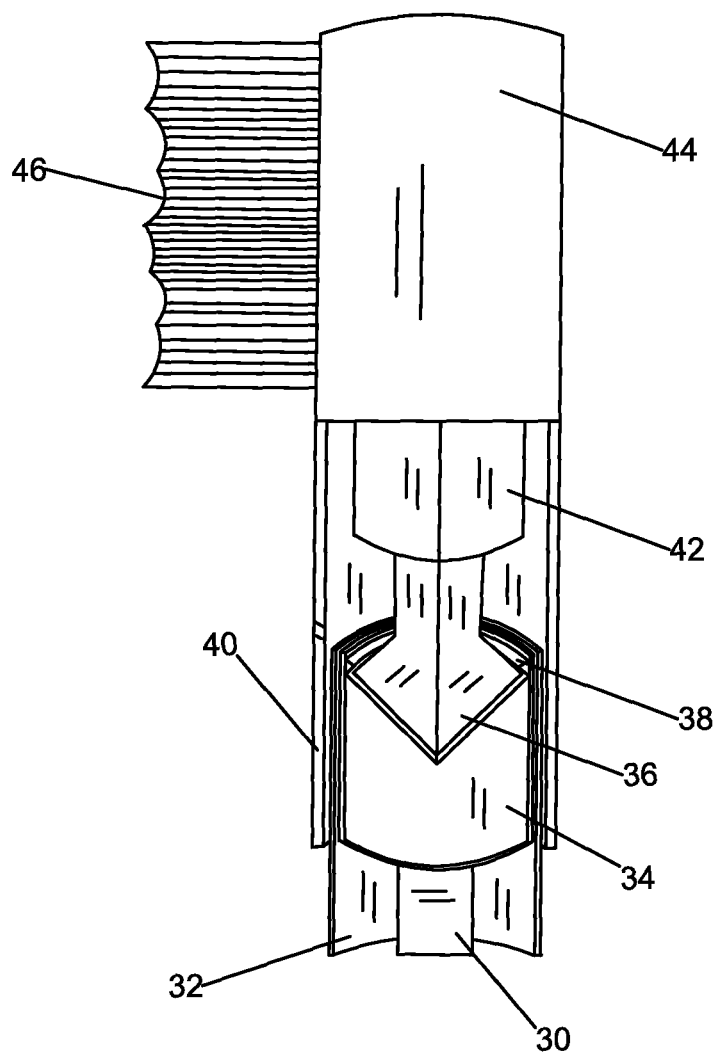
FIG. 2 shows a close up view of various components of the apparatus of FIG. 1.

FIG. 2 shows a close up view of various components of the apparatus 1 of FIG. 1. In particular FIG. 2 shows a close up view of the bottom axle 30, a section of the bottom cylinder 32, the square axle boot 34, the square axial leg 36, the bottom axle boot lip 38, a section of the tooth brush head cylinder 40, the square axle 42, the tooth brush head 44, and the tooth brush bristles 46.

Although the invention has been described by reference to particular illustrative embodiments thereof, many changes and modifications of the invention may become apparent to those skilled in the art without departing from the spirit and scope of the invention. It is therefore intended to include within this patent all such changes and modifications as may reasonably and properly be included within the scope of the present invention's contribution to the art.

I claim:

1. An apparatus comprising:
a toothbrush head;
toothbrush bristles fixed to the toothbrush head; and
means for moving the toothbrush head in up and down directions and for simultaneously rotating the tooth brush head in a plane which is perpendicular to the up and down directions; and
wherein the means for moving the toothbrush head in the up and down directions and for simultaneously rotating the tooth brush head in the plane which is perpendicular to the up and down directions includes a motor, a motor shaft, a disk, a swing arm, a post, and a pin;
wherein the apparatus is configured so that the motor rotates the motor shaft causing the disk to rotate which causes both the pin to move in the up and down directions and the swing arm to rotate in the plane which is perpendicular to the up and down directions;
wherein the movement of the pin up and down causes the post to move up and down which causes the toothbrush head to move up and down;
wherein the rotation of the swing arm in the plane which is perpendicular to the up and down directions causes the post to rotate in the plane which is perpendicular to the up and down directions which causes the toothbrush head to rotate in the plane which is perpendicular to the up and down directions; and wherein the disk includes first and second ramp portions which cause the pin to move in the up and down directions as the disk rotates.

2. The apparatus of claim 1 wherein
the post is elongated having a length and a width, with the length much greater than the width; and
wherein the post and the disk are situated with respect to each other so that a straight line running centrally through the post along the length of the post, does not pass through the disk.

3. The apparatus of claim 2 wherein
the pin physically contacts the disk to cause the pin to move in the up and down directions.

4. The apparatus of claim 2 wherein
wherein the means for moving the toothbrush head in the up and down directions and for simultaneously rotating the tooth brush head in the plane which is perpendicular to the up and down directions further includes a swing arm shaft;
and wherein the swing arm shaft is fixed to the disk and the swing arm shaft moves when the disk rotates to cause rotation of the swing arm.

5. The apparatus of claim 4 wherein
the swing arm shaft is inserted in a slot of the swing arm, and effectively slides in the slot of the swing arm when the disk rotates to cause rotation of the swing arm.

6. The apparatus of claim 1 wherein
the means for moving the toothbrush head in the up and down directions and for simultaneously rotating the tooth brush head in the plane which is perpendicular to the up and down directions further includes a swing arm shaft;
and wherein the swing arm shaft is fixed to the disk and the swing arm shaft moves with the disk when the disk rotates to cause rotation of the swing arm.

7. The apparatus of claim 6 wherein
the pin physically contacts the disk to cause the pin to move in the up and down directions.

8. The apparatus of claim 6 wherein
the swing arm shaft is inserted in a slot of the swing arm, and effectively slides in the slot of the swing arm when the disk rotates to cause rotation of the swing arm.

9. The apparatus of claim 1 wherein
the pin physically contacts the disk to cause the pin to move in the up and down directions.

10. A method comprising the steps of
using a motor to move a toothbrush head having toothbrush bristles fixed thereto in up and down directions and to simultaneously rotate the tooth brush head in a plane which is perpendicular to the up and down directions; and wherein
the motor turns a motor shaft which rotates a disk which causes both a pin to move in the up and down directions and a swing arm to rotate in the plane which is perpendicular to the up and down directions;
wherein the movement of the pin up and down causes a post to move up and down which causes the toothbrush head to move up and down; and
wherein the rotation of the swing arm in the plane which is perpendicular to the up and down directions causes the post to rotate in the plane which is perpendicular to the up and down directions which causes the toothbrush head to rotate in the plane which is perpendicular to the up and down directions
wherein the disk includes first and second ramp portions which cause the pin to move in the up and down directions as the disk rotates.

11. The method of claim 10 wherein the post is elongated having a length and a width, with the length much greater than the width; and wherein the post and the disk are situated with respect to each other so that a straight line running centrally through the post along the length of the post, does not pass through the disk.

12. The method of claim 11 wherein the pin physically contacts the disk to cause the pin to move in the up and down directions.

13. The method of claim 11 wherein wherein the means for moving the toothbrush head in the up and down directions and for simultaneously rotating the tooth brush head in the plane which is perpendicular to the up and down directions further includes a swing arm shaft;

and wherein the swing arm shaft is fixed to the disk and the swing arm shaft moves when the disk rotates to cause rotation of the swing arm.

14. The apparatus of claim 13 wherein the swing arm shaft is inserted in a slot of the swing arm, and effectively slides in the slot of the swing arm when the disk rotates to cause rotation of the swing arm.

15. The method of claim 10 wherein a swing arm shaft is fixed to the disk and the swing arm shaft moves with the disk when the disk rotates to cause rotation of the swing arm.

16. The method of claim 15 wherein the pin physically contacts the disk to cause the pin to move in the up and down directions.

17. The method of claim 15 wherein the swing arm shaft is inserted in a slot of the swing arm, and effectively slides in the slot of the swing arm when the disk rotates to cause rotation of the swing arm.

18. The method of claim 10 further comprising brushing a person's teeth with the toothbrush bristles.

19. The method of claim 10 wherein the pin physically contacts the disk to cause the pin to move in the up and down directions.

\* \* \* \* \*